US00PP19305P2

(12) United States Plant Patent
Yates

(10) Patent No.: US PP19,305 P2
(45) Date of Patent: Oct. 7, 2008

(54) ***VERONICA* PLANT NAMED 'YABPIN'**

(50) Latin Name: *Veronica hybrida*
Varietal Denomination: YABPIN

(76) Inventor: Frederic C. Yates, Holmes Chapel Rd., Somerford, Congleton Cheshire, CW12 4SP (GB)

( * ) Notice: Subject to any disclaimer, the term of this patent is extended or adjusted under 35 U.S.C. 154(b) by 0 days.

(21) Appl. No.: 11/888,253

(22) Filed: Jul. 31, 2007

(51) Int. Cl.
*A01H 5/00* (2006.01)

(52) U.S. Cl. ..... Plt./251

(58) Field of Classification Search ..... Plt./251
See application file for complete search history.

*Primary Examiner*—Kent L. Bell
*Assistant Examiner*—June Hwu
(74) *Attorney, Agent, or Firm*—Penny J. Aguirre

(57) ABSTRACT

A new cultivar of *Veronica* of hybrid origin, *Veronica* 'YABPIN', characterized by its compact dense plant habit, its abundance of branched upright flowering stems of self cleaning pink flowers and its resistance to powdery mildew and other fungal diseases.

2 Drawing Sheets

RELATED APPLICATIONS

This application is co-pending with U.S. Plant patent application No. 09/520,231 filed for a cultivar derived from the same parentage entitled *Veronica* Plant Named 'YABBLU'.

Botanical classification: *Veronica hybrida.*

Cultivar designation: 'YABPIN'.

BACKGROUND OF THE INVENTION

The present invention relates to a new and distinct cultivar of *Veronica,* botanically a hybrid known as *Veronica* 'YABPIN' and will be referred to hereafter by its cultivar name, 'YABPIN'.

The new cultivar was derived from a controlled breeding program conducted by the inventor at his nursery in Congleton, Cheshire, U.K. The overall purpose of the breeding program is to make selections of *Veronica* plants that exhibit compact plant habits, are floriferous, and exhibit mildew resistance. 'YABPIN' was selected as a single plant derived from a cross made in 2002 between an unnamed female parent of a *Veronica* of unknown parentage and botanical origin and a male a parent selected from the seed strain *Veronica spicata* 'Sightseeing' (not patented).

Asexual reproduction of the new cultivar was first accomplished by terminal stem cuttings in Congleton, Cheshire, U.K. in 2003 by the inventor. It has been determined that the characteristics of this cultivar are stable and are reproduced true to type in successive generations.

SUMMARY OF THE INVENTION

The following traits have been repeatedly observed and represent the characteristics of the new cultivar, which in combination distinguish 'YABPIN' as a new and distinct cultivar of *Veronica.*

1. 'YABBLU' exhibits a compact plant habit due to a high degree of adventititous shoot development.
2. 'YABBLU' exhibits a floriferous habit with branched, upright flower stems.

3. 'YABBLU' exhibits flowers that are self-cleaning as the flower scape internode length allows for spent flowers to drop; a quality that is not typical for *Veronica* cultivars.
4. 'YABBLU' exhibits resistance to powdery mildew and other fungal diseases.
5. 'YABPIN' exhibits pink flowers.

'YABPIN' differs from its female parent in being more robust, more upright, and by being more floriferous. 'YABPIN' differs from its male parent, a 'Sightseeing' selection, in being more reliably perennial, by having denser basal growth and better mildew resistance. The 'Sightseeing' hybrids are the closest comparison plants known to the inventor in addition to 'YABBLU' from the same breeding program. 'YABPIN' differs from 'YABBLU' in having pink flowers. 'YABPIN' can also be compared to *Veronica spicata* 'Glory' (U.S. Plant Pat. No. 18,932). 'YABPIN' is similar to 'Glory' in general habit, however 'YABPIN' is more compact, has flowers that are self cleaning, has a greater resistance to powdery mildew and other fungal diseases, and has pink flowers rather than blue.

BRIEF DESCRIPTION OF THE DRAWING

The accompanying colored photographs illustrate the overall appearance and distinct characteristics of the new *Veronica.* The photographs in FIG. 1 and FIG. 2 were taken in June 2006 of a plant approximately 9 months in age grown from 4 small plugs in a 12 cm container in Banbury, Oxfordshire, U.K.

The photograph in FIG. 1 provides a side view of 'YABPIN' in bloom.

Figure 1:
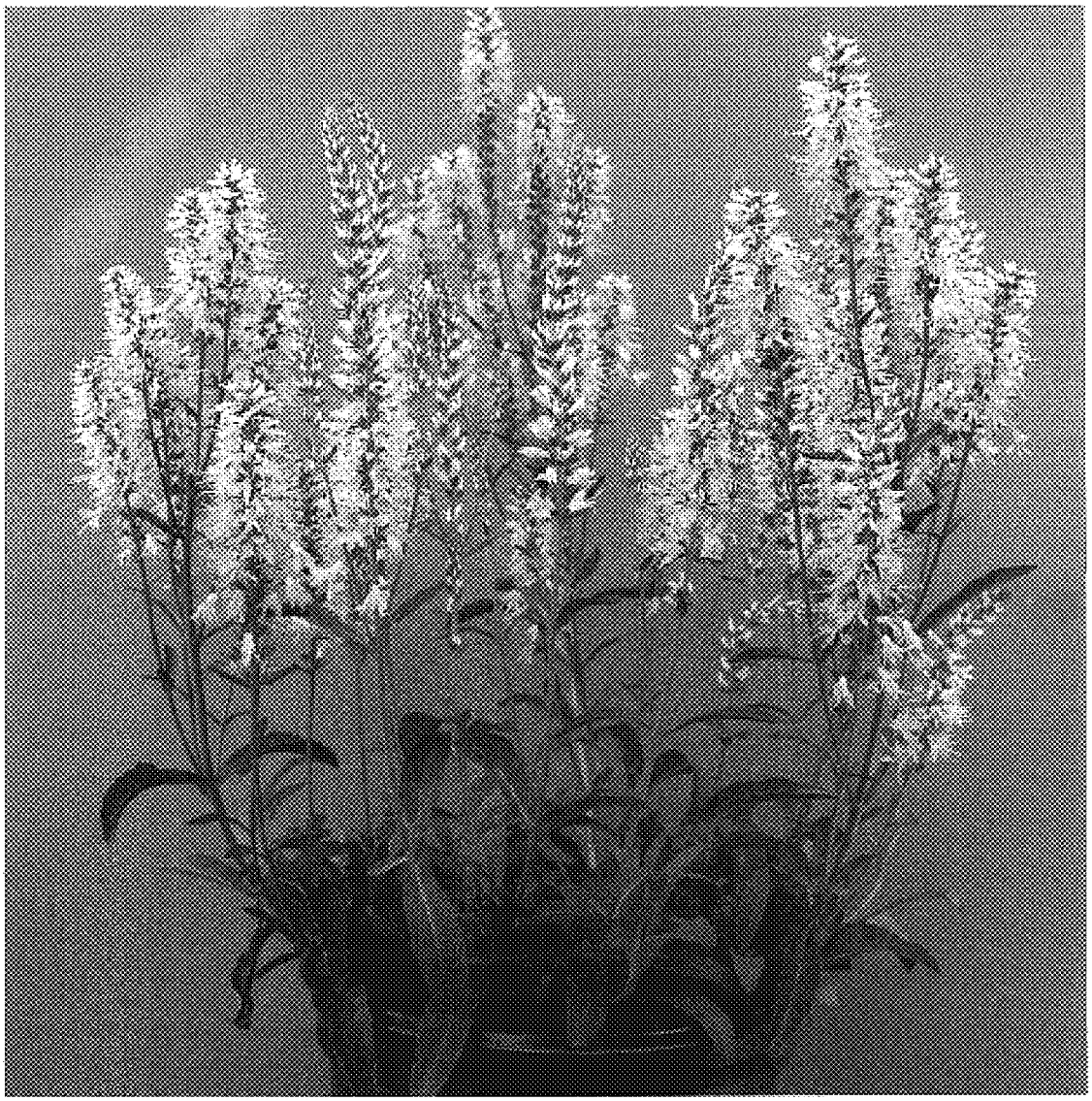
Figure 2:
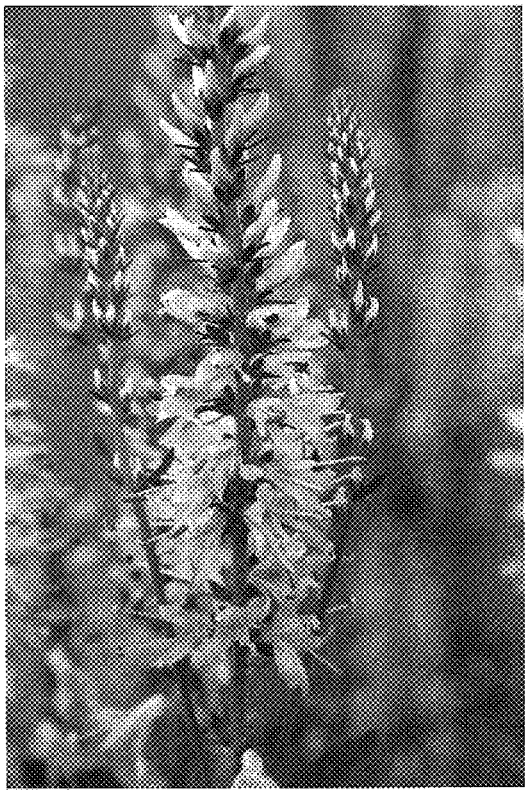

The photograph in FIG. 2 provides a close-up view of the flowers of 'YABPIN'.

Figure 3:
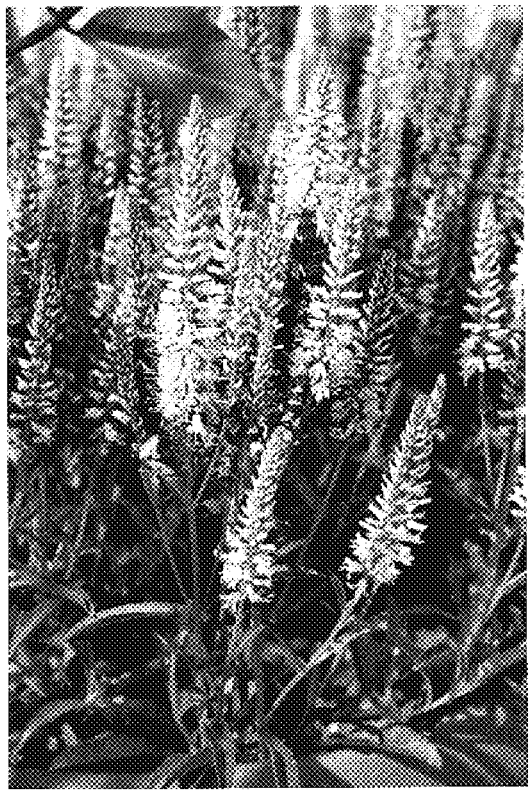

The photograph in FIG. 3 is included to show the adventitious shoot development of plugs grown for 6 months over the winter months from October to April.

The colors in the photographs are as close as possible with the photographic and printing technology utilized. The color values cited in the detailed botanical description accurately describe the colors of the new *Veronica.*

DETAILED BOTANICAL DESCRIPTION OF THE PLANT

The following is a detailed description of plants of the new cultivar approximately 9 months in age as grown in one-liter containers under greenhouse conditions with ambient light in Cambridgeshire, U.K. The phenotype of the new cultivar may vary with variations in environmental, climatic, and cultural conditions, as it has not been tested under all possible environmental conditions. The color determination is in accordance with the 2001 R.H.S. Colour Chart of The Royal Horticultural Society, London, England, except where general color terms of ordinary dictionary significance are used.

Botanical classification: 'YABPIN' is a cultivar of hybrid origin of *Veronica* (unknown hybrid *V. spicata*).

General plant characteristics:

*Plant type.*—Evergreen perennial, grown for use in garden borders and patio containers.

*Plant habit.*—Compact and upright.

*Flowering period.*—From May to August under U.K. conditions.

*Height and spread.*—Reaches about 27 cm in height and spread is indeterminate.

*Cold hardiness.*—U.S.D.A. Zone 4.

*Culture.*—Tolerant of most soil types and grows well in full sun to partial shade under U.K. conditions.

*Diseases.*—Resistance to powdery mildew and other fungal disease.

*Root description.*—Fibrous.

Growth and propagation:

*Growth rate.*—Typical vigor for the species but with more compact growth.

*Propagation.*—Terminal stem cuttings.

*Time required for root development.*—About 14 days at 20° C.

*Time required for root development.*—8 weeks to reach commercial size.

*Vigor.*—Moderately vigorous in spite of compact habit.

Stem description (flowering):

*Stem size.*—Average of 25 cm in length and 2 mm in width.

*Stem shape.*—Round.

*Stem color.*—Between 139B and 139C.

*Stem surface.*—Finely pubescent, lenticels absent.

*Internode length.*—Average of 2.5 cm.

*Branching habit.*—Branched flowering stems (5 to 10 laterals) arise from a mat of congested basal stems.

*Branching angle at emergence.*—About 30° relative to the stem.

Foliage description:

*Leaf shape.*—Obovate to elliptic.

*Leaf division.*—Entire.

*Leaf base.*—Acuminate.

*Leaf apex.*—Obtuse.

*Leaf venation.*—Pinnate, color nearest 143D on upper and lower surface.

*Leaf margins.*—Crenate.

*Leaf attachment.*—Petiolate.

*Leaf arrangement.*—Opposite.

*Leaf surface.*—Upper surface; sparsely pubescent, lower surface; sparsely pubescent on blade and moderately pubescent on veins.

*Leaf color.*—Upper surface 139A and lower surface between 137C and 137D.

*Leaf size.*—Average of 4 cm in length and 1.4 cm in width.

*Leaf fragrance.*—None.

*Petioles.*—About 1.1 cm in length and 2 mm in width, surface is finely pubescent, color is 143C, stipules are absent.

Flower description:

*Inflorescene type.*—Raceme of single funnel-shaped flowers.

*Inflorescence size.*—About 8 mm in length and 2 cm in width.

*Flower persistence.*—Self-cleaning.

*Flower shape.*—Funnel formed.

*Flower fragrance.*—None.

*Flower quantity.*—Between 50 to 100 per stem.

*Flower arrangement.*—Positioned separately or up to 5 in a whorl, internode length on peduncle ranges from 0.5 to 5 mm.

*Flower aspect.*—About a 45° angle to upright prior to opening and open to horizontal to slightly downward, horizontal on average.

*Flower fragrance.*—None detected.

*Flower lastingness.*—About 6 to 8 days per flower.

*Flower size.*—About 6 mm in depth and 5 mm in diameter.

*Peduncles.*—About 2.5 cm in length below flowers and 1.5 mm in width, between 139B and 139C in color, surface is finely pubescence, round in shape.

*Pedicels.*—Average of 0.5 mm in length and 0.3 mm in width, between 139B and 139C in color, surface is sparsely pubescent.

*Flower buds.*—Elongated ovoid in shape, average of 4 mm in length and 1 mm in diameter, nearest 75C in color.

*Calyx.*—Lacking tube with sepals held almost erect, about 2 mm in length and 1 mm in width.

*Sepals.*—4, narrow triangular-ovate in shape, margin is entire, apex is acute, base is fused, surface is covered with very fine white hairs, color of upper and lower surface is 139B, <1 mm in width and 2 mm in length.

*Corolla.*—Funnel-formed with petals fused into tube towards base, 6 mm in length and 5 mm in width.

*Petals.*—4, tube portion: about 1.5 mm in length and width and nearest 75D in color with a glabrous, lobes: broadly linear in shape, margin is entire, apex is rounded, upper and lower surface is glabrous, color of upper surface and lower surface is between 75B and 75C about 4 mm in length and 1.5 mm in width.

Reproductive organs:

*Gynoecium.*—1 Pistil, stigma and style are not distinguishable, filiform in shape, about 7 mm in length and <0.5 mm in width and N81B in color becoming paler towards base, ovary is superior, ovoid in shape, about 1 mm in length and 0.7 mm in width and 144D in color.

*Androcoecium.*—2 stamens, anthers are ovoid in shape, about 1 mm in length and <0.5 mm in width and N182D in color, filaments are about 5 mm in length and about 0.5 mm in width and between 75B and 75C in color, pollen is moderate in quantity and 160C in color.

*Seed.*—4 or less, laterally compressed ovoid in shape, about 1 mm in length and 0.7 mm in width and N199C in color.

I claim:

1. A new and distinct cultivar of *Veronica* plant named 'YABPIN' as herein illustrated and described.

* * * * *